(12) United States Patent
McCorkle

(10) Patent No.: US 7,547,390 B2
(45) Date of Patent: Jun. 16, 2009

(54) SYSTEM OF CONVERTING ANIMAL WASTES TO ENERGY AND USEFUL BY-PRODUCTS

(75) Inventor: Stephen R. McCorkle, Westlake Village, CA (US)

(73) Assignee: Agricultural Waste Solutions, Inc., Thousand Oaks, CA (US)

( * ) Notice: Subject to any disclaimer, the term of this patent is extended or adjusted under 35 U.S.C. 154(b) by 628 days.

(21) Appl. No.: 11/099,389

(22) Filed: Apr. 4, 2005

(65) Prior Publication Data

US 2005/0218087 A1    Oct. 6, 2005

Related U.S. Application Data

(60) Provisional application No. 60/560,409, filed on Apr. 6, 2004.

(51) Int. Cl.
*C02F 1/54* (2006.01)
(52) U.S. Cl. ............... 210/173; 48/197 R; 210/202; 210/251; 210/257.1
(58) Field of Classification Search ............ 210/173
See application file for complete search history.

(56) References Cited

U.S. PATENT DOCUMENTS

| 3,537,659 | A | * | 11/1970 | Vagedes | ............ 241/46.02 |
| 3,838,199 | A | * | 9/1974 | Coe et al. | ............ 426/55 |
| 3,973,043 | A | * | 8/1976 | Lynn | ............ 426/55 |
| 4,198,211 | A | * | 4/1980 | Shattock | ............ 48/197 A |
| 4,250,023 | A | * | 2/1981 | Samis et al. | ............ 241/20 |
| 4,857,458 | A | * | 8/1989 | Nobilet et al. | ............ 435/290.4 |
| 6,083,386 | A | * | 7/2000 | Lloyd | ............ 210/195.1 |
| 6,190,566 | B1 | * | 2/2001 | Kolber | ............ 210/744 |
| 6,299,774 | B1 | * | 10/2001 | Ainsworth et al. | ............ 210/603 |
| 6,470,828 | B1 | | 10/2002 | Townsend et al. | |
| 6,521,129 | B1 | * | 2/2003 | Stamper et al. | ............ 210/603 |
| 6,863,826 | B2 | | 3/2005 | Sheets | |
| 7,005,068 | B2 | * | 2/2006 | Hoffland | ............ 210/603 |
| 7,015,028 | B2 | * | 3/2006 | Choate et al. | ............ 435/262.5 |
| 7,105,088 | B2 | * | 9/2006 | Schien et al. | ............ 210/188 |

* cited by examiner

*Primary Examiner*—Peter A Hruskoci
(74) *Attorney, Agent, or Firm*—Malcolm J. Romano

(57) ABSTRACT

A system and method for converting animal waste, in the form of waste slurry, to energy and useful byproducts. A screen mesh filters out large objects from waste slurry and the filtered slurry is chopped and fragmented to reduce binding of fibrous materials. The fragmented slurry is mixed at a rate to maintain solids in the fragmented slurry in suspension while minimizing aeration and turbulence within the mixing unit. A solids recovery unit recovers about 95% of the suspended solids. A polymer is introduced into the solids recovery unit for providing agglomeration of solids particles. The recovered solids are gasified to produce at least methane/ethane gas. The produced gas is provided to an energy production unit to generate electrical and/or heat energy. Liquid remaining after the solids recovery is treated to remove undesirable contaminants to an extent in compliance with water quality standards set for animal waste flushing, animal washing and animal drinking water, as the case may be.

19 Claims, 2 Drawing Sheets

SYSTEM OF CONVERTING ANIMAL WASTES TO ENERGY AND USEFUL BY-PRODUCTS

REFERENCE TO PRIORITY APPLICATIONS

This application claims the benefit of and the priority date from Provisional Application Ser. No. 60/560,409 entitled "System for Converting Animal Wastes to Energy and Useful By-Products" filed Apr. 6, 2004, the contents of which are incorporated herein in its entirety, by reference.

FIELD OF THE INVENTION

The invention relates generally to processing animal wastes, principally in the form of waste slurry, to produce useful by-products such as treated water for irrigation, barn flushing, animal drinking water as well as organic solids for fertilizers and feedstock for gasification to produce gas for heat and electricity generation or for alternative fuel uses.

BACKGROUND OF THE INVENTION

The animal feeding industry, principally swine and dairy, by virtue of the associated animal wastes, has been recognized as the most significant contributor to water pollution in the world. In December 2002, the United States Environmental Protection Agency (EPA) and Canada passed new legislation ("The New Rule") initially requiring over 12,000 large producers to obtain special permits that mandate remediation of the wastes they generate. Most of these producers presently have no economically viable methods to qualify for these permits and in many cases industry expansion has been frozen and producers are forced to operate below capacity. The animal wastes from large swine and dairy farms, known as CAFO'S (Concentrated Animal Feeding Operations) in North America, range in the billions of pounds and are a combination of urine, feces and wash water. These wastes typically are piped to a "lagoon", a pit used to hold wastes for up to about six months. The more dense solids fall to the bottom of the lagoon where they receive minimal treatment and have to be excavated and disposed of periodically. An accepted practice for many years is to spray the liquid portion of the wastes over adjoining land parcels and fields as a fertilizer. The liquid is rich in the nutrients of phosphorous, potassium, and nitrogen which are aids to crop growth. As a result of such spraying practices, farm fields in over 500 U.S. counties have become overburdened with these nutrients such that the crops can no longer absorb them. When this occurs, the excess nutrients runoff and enter drinking water wells, streams and coastal bays.

SUMMARY

An embodiment of the invention comprises a screen mesh sized to screen out relatively large objects in waste slurry flushed from an animal barn or retention area, a chopper unit configured to receive the screened waste slurry and fragment the waste slurry for reducing the binding of fibrous materials contained within the screened waste slurry, a mixing tank configured to receive the fragmented waste slurry and for mixing the fragmented waste slurry so as to maintain solids in suspension within the fragmented waste slurry and a solids recovery unit configured to remove at least a predetermined amount of suspended solids from the fragmented waste slurry thereby producing a solids output and a liquid output. An additive, as for example, one selected from the group consisting of polyacrylamide, ferric chloride and ferric sulfate, is introduced into the solids recovery unit for providing agglomeration of solids particles.

Another embodiment of the invention includes a gas production unit configured to receive the solids output and produce gas therefrom. Preferably, the gas produced is methane/ethane gas. Yet another embodiment includes an energy production unit configured to generate electrical and/or heat energy from the produced gas. Yet another embodiment includes a water treatment unit configured to remove undesirable contaminants from the liquids output. Particular contaminants are selected from but not limited to the group consisting of nutrients, pathogens, viruses and coliforms. Coliforms consist of a related group of bacteria species and are found typically in human and animal wastes and normally are fecal in origin. *Escherichia coli* 0157: H7, otherwise referred to as, *E. coli*, is a coliform species found in the intestinal tract of warm-blooded animals. Its presence can be indicative of fresh pollution from human or animal waste. Although normally benign, some *E. coli* strains may be deadly. The embodiments of the present invention address the necessity of reducing the *E. coli* content of processed animal wastes to acceptable levels.

Another embodiment is a process or method of converting animal waste in the form of waste slurry into energy and useful byproducts comprising passing the waste slurry through a mesh screen to filter out relatively large objects from the waste slurry, fragmenting the filtered waste slurry for reducing binding of fibrous materials contained within the filtered waste slurry, mixing the fragmented waste slurry to maintain solids in suspension within the fragmented waste slurry and removing at least a minimum amount of suspended solids from the fragmented waste slurry to produce a solids output and a liquid output. Yet another embodiment includes removing at least 75% of the solids content from the fragmented waste slurry. Yet another embodiment includes heating the removed solids content to reduce solids moisture content to about 50%. Yet another embodiment includes gasifying the reduced moisture content solids to produce at least methane/ethane gas. Yet another embodiment includes exhausting the produced gas into the atmosphere in compliance with established air quality standards. Yet another embodiment includes producing electrical and/or heat energy from the produced gas. Yet another embodiment includes removing undesirable contaminants from the liquid output to the extent required to comply with predefined water quality standards for washing down the growing barns and/or safer irrigation water.

DETAILED DESCRIPTION

Figure 1:
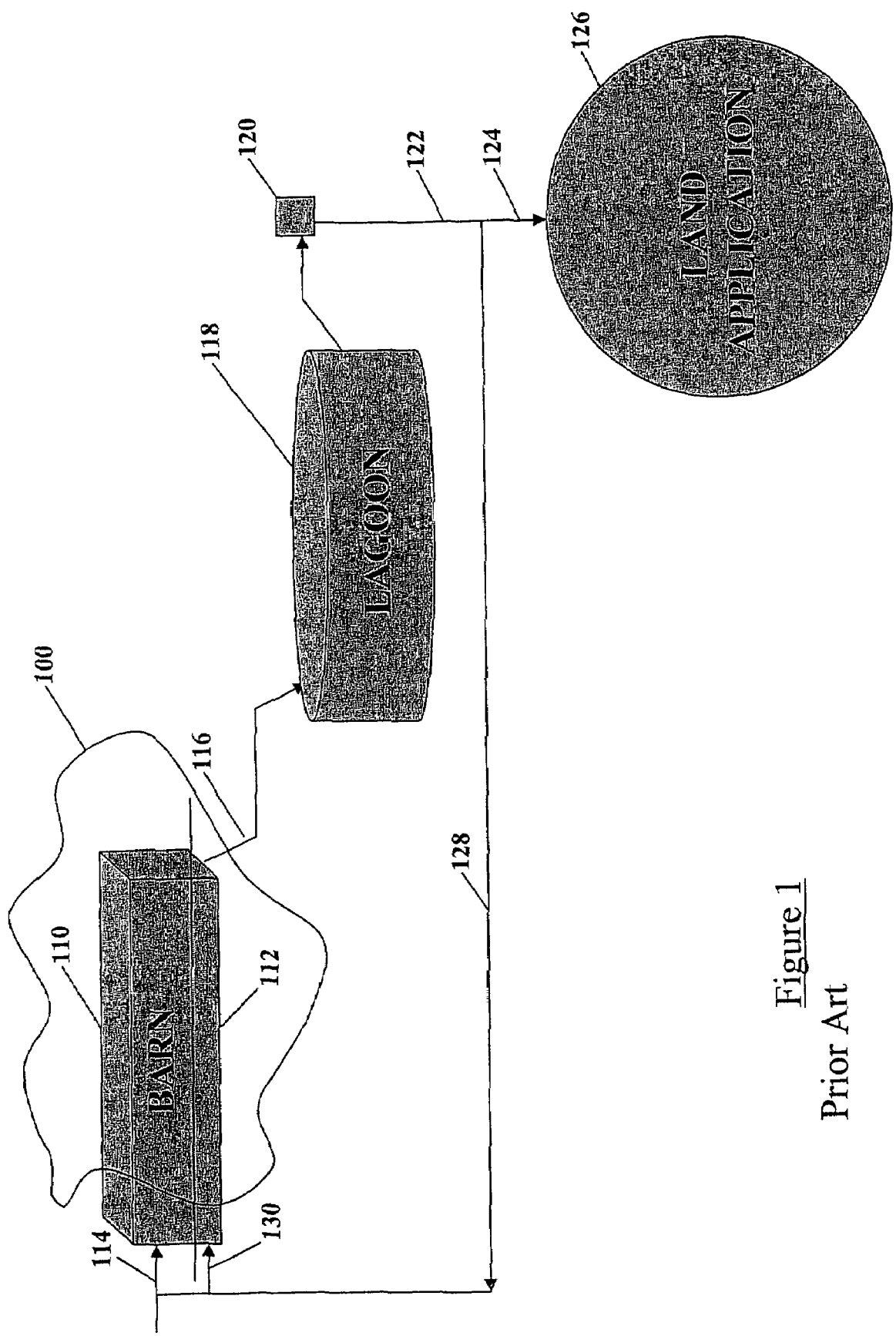
FIG. 1 is a schematic view of a conventional animal waste removal and management system utilizing a barn and a disposal lagoon.

Prior to a discussion of embodiments of the invention it is instructive to appreciate an example of a conventional animal waste removal system utilizing a flush system and technique. Referring to FIG. 1, an animal barn or other confinement structure 110 includes under floor level waste slurry pits 112. The slurry pits 112 collect various types of animal waste elements such as urine, feces and perhaps even small fetuses.

Water, presumably meeting animal wash and cooling purity standards, is pumped through clean water inlet 114 for animal washing activities and is also mixed with recycled lagoon (118) water and flushed through the waste slurry pits 112. The flushed waste slurry is piped directly into lagoon 118 through conduit 116. Typically, the waste slurry comprises about 0.5 to 3% solids content. Water is drawn from lagoon 118 by means of water pump 120 and recycled through conduit 128 back to the slurry pits 112 to further flush the slurry. Alternately, diluted waste slurry may be diverted, through conduit 124 for land application purposes.

Figure 2:
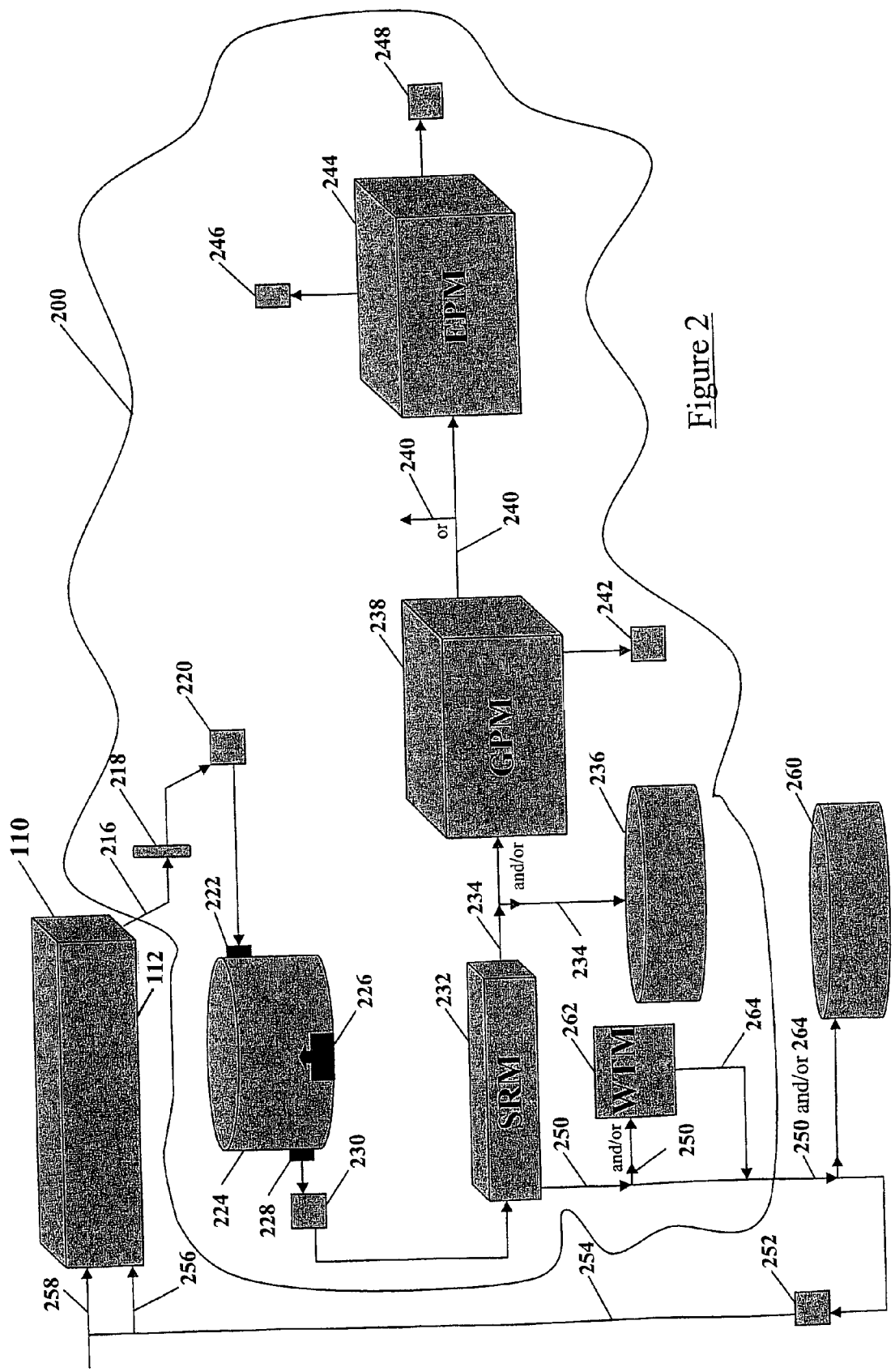
FIG. 2 is a schematic view of an animal waste removal and management system configured in accordance to an embodiment of the present invention.

From the foregoing, it should be apparent that much more attention need be devoted to the major re-thinking of animal waste processing and disposal. Accordingly, reference is made to FIG. 2, illustrating an embodiment 200 of the invention. Structure 110 may be similar to the animal barn referred to in FIG. 1 wherein confined animals may be housed, fed, milked as in the case of dairy cows, washed and kept under cover. Waste material excreted by the animals, drops into and is collected in slurry pits 112. Conduit 216 carries the collected waste slurry to a mechanical screen unit 218 having a mesh size of approximately 2 inches to capture relatively large objects such as trash and animal fetuses. It should be understood that the screen mesh size may be selected of differing dimensions according to a desired filtration capability. It should also be understood that in those applications where the slurry pits contain a screening device or when the CAFO's, for example, include a screening operation in their waste management process, then in such case, the necessity of mechanical screen unit 218 is obviated. The screened waste slurry proceeds to a chopper pump 220 for fragmenting the slurry into smaller aggregates in order to reduce the binding effect of larger fibrous materials in the screened waste slurry. The pumping rate of chopper pump 220 is selected dependent upon waste slurry processing demands. For example, a barn sized to accommodate 4000 swine or 500 milking cows, which represents a small concentrated animal feeding operation (CAFO) could require a flow rate of about 20 gallons per minute for proper flushing of waste slurry from barn 110. The specifications for chopper pump 220 are selected for processing the screened waste slurry at a rate at least as fast as the flow rate for the particular CAFO of interest.

The fragmented waste slurry is then fed to a wet well or mixing tank 224 through a mixing tank inlet screen 222. The mixing tank includes a mixing device designed to maintain the solids in the fragmented waste slurry in suspension with a minimum of mixing turbulence. As an example, for the above flow rates, a 20 hp motor with a 4 foot diameter impeller provides the intended function with minimal aeration and physical damage to mixing tank contents as it is filling. The waste slurry is discharged from mixing tank 224 through outlet 228 under the action of discharge pump 230. It is to be understood that in those applications where the CAFO's, for example, include a mixing operation in their waste management process, then in such case, the necessity of mixing tank 224 is obviated.

The discharge from mixing tank 224 is fed to solids recovery unit 232, a centrifuge separation device capable of separating apart the suspended solids content and the liquid content of the fragmented waste slurry. An additive such as polyacrylamide, ferric chloride, alum or ferric sulfate is introduced into the solids recovery unit to provide very effective agglomeration of solids particles. A typical particle size for the suspended solids is about 40 microns in diameter and the solids recovery unit 232 breaks apart the solids particles to within the range of about 5 to 10 microns in diameter. The solids recovery unit 232 removes about 75% to 98% of the suspended solids from the fragmented waste slurry. Under normal operation, solids removal is at least a minimum of 95% of the suspended solids. Furthermore, the solids recovery unit produces a solids output having about 60% to 80% moisture and under normal operation a maximum of about 75% moisture. Advantageously, the removal of 95% of the suspended solids by the solids recovery unit 232 also results in the removal of sufficient nutrients identified by the Environmental Protection Agency's "New Rule" from the liquid content to reduce the typical land area requirement for irrigation by about 90%. Commercially available units, such as the Westfalia Centrisys centrifuge may be utilized to produce treated and dewatered solids.

At the user's choice, the separated liquid content is carried by conduit 250 to either water treatment module (WTM)/unit 262 or under the action of pump 252, back to the barn 110 as recycled flush liquid for flushing the slurry pits 112. Further at the user's discretion, treated liquid can be directly utilized by a storage and irrigation system 260 to be used to irrigate desired land parcels. The water treatment unit 262 receives the separated liquid content and processes it to further remove remaining nutrients, pathogens, viruses and coliforms. Commercially available units, such as the MEMCOR Membrane Biological Reactor, may be utilized to produce water complying with purity standards established for animal drinking water. Alternately, water may be produced just below animal drinking quality standards, but sufficiently high to comply with quality standards established for washing down the animals, recycling animal wastes and which would require minimal land acreage for irrigation. Advantageously, the water treatment unit 262 is very cost effective compared to conventional water treatment or water "polishing" systems in that the received liquid content is approximately 95% solids free and mostly nutrient free as a result of the waste slurry processing in the solids recovery unit 232. Furthermore, due to the purity of the water produced, the high capital and operating costs of lagoons, irrigation and crop growing, is markedly reduced.

At the user's choice, the solids output from the solids recovery unit 232 is conveyed by conveyance device 234 to either a solids storage bin 236 or to gas production module (GPM)/unit 238. Depending upon the nature of the solids output, the solids conveyed may be at a rate, for example, of about 1000 pounds per hour. Obviously, a smaller or greater amount of solids conveyed per hour, depends upon the capacity of selected system units. The solids conveyed to storage bin 236 have a high organic content and the bin may be either a permanent structure or may be mobile and adapted for movement from one location to another, which facilitates being filled at one location and emptied at another location. The solids output have a market value as fertilizer for spreading over crop producing fields, either under the control of the user or to be sold for use by others. In this regard, an embodiment of the invention provides a financial return to the user in addition to the benefit of efficient animal waste removal and management.

At the user's choice, the solids output may be conveyed to gas production unit 238 configured for gasification of the received solids output. The gas production unit 238 includes a heated input hopper (not shown) that serves to heat the received solids output to reduce the solids moisture to approximately 50% during a pre-gasification time of about one hour. The solids output is converted primarily to methane/ethane gas that has a heating value of about 600 to 1200 BTU. At the user's choice, and due to the nature of the gas produced, the gas may be flared into the atmosphere without violating existing air quality standards. As a by-product of the gas production, a small amount of ash is produced and collected in receptacle 242. A typical ash production rate is about 50 to 100 pounds per hour. Obviously, ash production rates depend upon processing capacities of the various processing units comprising the disclosed system and the amount of ingredients contained in the waste stream. The ash is a valuable by-product as an additive that can be either added to animal feed or marketed separately. Again and in this regard, an embodiment of the invention provides a further financial return to the user in addition to the benefit of efficient animal waste removal and management. The gas production unit 238 is configured to minimize ash production and thereby reduce the number of ancillary processes and removal steps for ash management while increasing the heating value and volume of the produced gas. A commercially available gasification unit is the Brookes Gasification Process unit from BGP, Inc. of Scarborough, Ontario, Canada.

At the user's choice, the un-flared produced gas may be piped through conduit 240 to the energy production module (EPM)/unit 244. The energy production unit 244 is preferably, but not necessarily, a micro-turbine configured to produce either or both, electrical energy (shown as block 246) and heat energy (shown as block 248). Typical energy production for the system disclosed herein is about 150 to 200 kilowatt-hours electrical energy and the energy production unit is about 50 to 65% efficient when combining both electrical and heat energy. The user may choose to apply the produced energy for its own applications for added convenience and to reduce site operating costs, including overall animal waste removal and management costs. Alternately, the user may choose to market the produced energy and realize a financial return as an offset to system operation costs. A commercially available energy production unit is the CP 30, available from the Capstone Turbine Corporation of Chatsworth, Calif.

Although embodiments of the invention have been described, it is to be recognized that modifications may be made without departing from the novel concepts disclosed herein. Accordingly, it is intended that the scope of the invention be determined by the appended claims and their equivalents.

What is claimed is:

1. A system for converting animal waste, in the form of waste slurry, to useful by-products comprising:
    a chopper unit configured to receive waste slurry from a waste slurry source and fragment the waste slurry for reducing binding of fibrous materials contained within the waste slurry;
    a mixing tank configured to receive the fragmented waste slurry and for mixing the fragmented waste slurry so as to maintain solids in suspension within the fragmented waste slurry, said mixing tank including a mixing device configured for mixing the fragmented waste slurry to maintain the solids in suspension with minimal mixing turbulence;
    a solids recovery unit configured to remove at least a predetermined minimum amount of solids from the fragmented waste slurry producing thereby a solids output and a liquid output, wherein the minimum amount of recovered solids is at least 75% of the solid content of the waste slurry; and a gas production unit comprising an input hopper adapted to receive the solids output, the gas production unit configured to produce methane/ethane gas and ash from the received solids output.

2. The system of claim 1, wherein the solids recovery unit is configured to produce a solids output having a moisture content in the range of about 60% to 80%.

3. The system of claim 2, further comprising a solids storage bin sized to store the solids output for future usage and/or as feedstock for gasification.

4. The system of claim 2, further comprising a water treatment unit adapted to remove undesirable contaminants from the liquid output.

5. The system of claim 4, wherein the removed contaminants are selected from the group consisting of nutrients, pathogens, viruses and coliforms.

6. The system of claim 4, wherein the undesirable contaminants are removed to the extent required to comply with predefined water quality standards for water used for washing down animals and/or for flushing animal wastes.

7. The system of claim 4, wherein the contaminants are removed to the extent required to comply with water quality standards for animal drinking water.

8. The system of claim 1, wherein the gas production unit is configured to produce gas having a heating value in the range of about 600 to 1200 BTU.

9. The system of claim 1, wherein the gas production unit is adapted to exhaust the produced gas into the atmosphere in a manner complying with pre-defined environmental air quality standards.

10. The system of claim 1, wherein the gas production unit further comprises a heated input hopper adapted to reduce solids moisture content to about 50%.

11. The system of claim 1, further comprising an energy production unit adapted to generate electrical energy from the gas produced from the gas production unit.

12. The system of claim 11, wherein the electrical energy produced by the energy production unit is about 150 to 200 kilowatt-hours.

13. The system of claim 11 wherein the energy production unit is a micro-turbine configured to produce electrical energy.

14. The system of claim 1, further comprising an energy production unit adapted to generate heat energy from the gas produced from the gas production unit.

15. The system of claim 14, wherein the energy production unit is a micro-turbine configured to produce heat energy.

16. The system of claim 1 further comprising a screen mesh interposed between the waste slurry source and the chopper unit configured and sized to screen out relatively large objects from the waste slurry.

17. The system of claim 1, wherein said mixing device comprises an impeller configured to cause minimal aeration to the fragmented waste slurry during mixing.

18. The system of claim 1, further comprising means for introducing an additive selected from the group consisting of polyacrylamide, ferric chloride and ferric sulfate into the solids recovery unit for providing agglomeration of solids particles.

19. A system for converting animal waste, in the form of waste slurry, to energy and useful by-products comprising:
    a screen mesh configured and sized to screen out relatively large objects from the waste slurry;
    a chopper unit configured to receive the screened waste slurry and fragment the screened waste slurry for reducing binding of fibrous materials contained within the screened waste slurry;
    a mixing tank configured to receive the fragmented waste slurry and for mixing the fragmented waste slurry so as to maintain solids in suspension within the fragmented waste slurry, said mixing tank including a mixing device configured for mixing the fragmented waste slurry to maintain the solids in suspension with minimal mixing turbulence; and a solids recovery unit configured to remove at least a predetermined minimum amount of suspended solids from the fragmented waste slurry producing thereby a solids output and a liquid output, wherein the minimum amount of recovered solids is at least 75% of the solid content of the waste slurry; and a gas production unit comprising an input hopper adapted to receive the solids output, the gas production unit configured to produce methane/ethane gas and ash from the received solids output.

* * * * *